United States Patent [19]

Bogossian

[11] 4,456,030
[45] Jun. 26, 1984

[54] LINEAR METERING VALVE FOR TUBES
[75] Inventor: Armen Bogossian, Teaneck, N.J.
[73] Assignee: Flow Technology Corporation, Oakland, N.J.
[21] Appl. No.: 293,246
[22] Filed: Aug. 17, 1981
[51] Int. Cl.³ ................................ F16L 55/14
[52] U.S. Cl. ..................... 137/614.11; 251/7; 251/8
[58] Field of Search ............... 251/7, 8; 137/614.11
[56] References Cited
U.S. PATENT DOCUMENTS 2,092,401  9/1937  Miller ............................ 251/7
3,497,175  2/1970  Koland .......................... 251/8
3,627,383  12/1971 Adler ............................ 251/8
3,759,483  9/1973  Baxter ........................... 251/7
3,774,876  11/1973 Melsheimer .................... 251/8

Primary Examiner—A. Michael Chambers
Attorney, Agent, or Firm—Kenyon & Kenyon

[57] ABSTRACT

The valve can be slid over a tube for feeding intravenous fluids to a patient and is manually operable with one hand to control the flow through the tube. A rotatable spindle moves a wedge-shaped draw bar to force a platten with protuberances against the tube to reduce the cross-sectional areas of the tube at multiple points for sensitive metering action.

16 Claims, 8 Drawing Figures

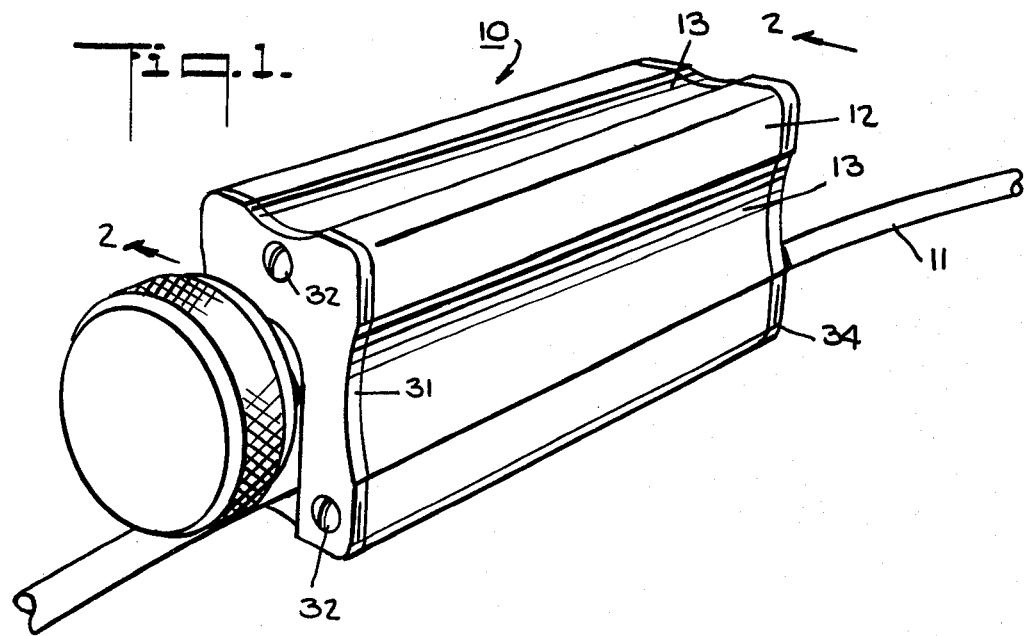
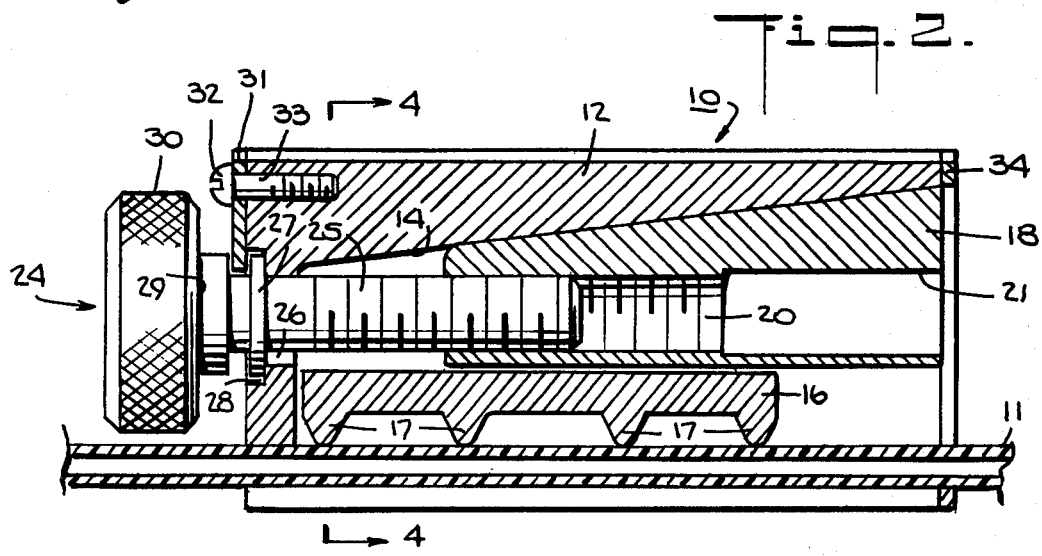
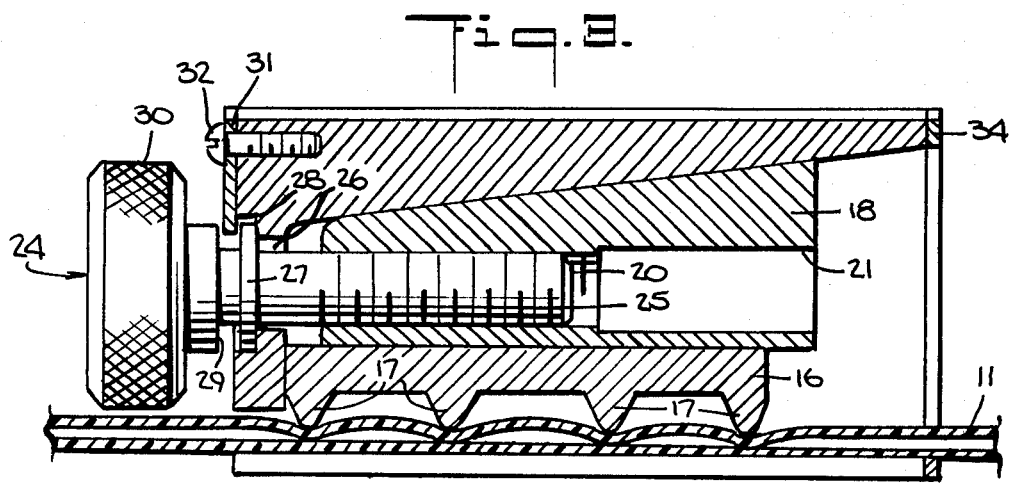

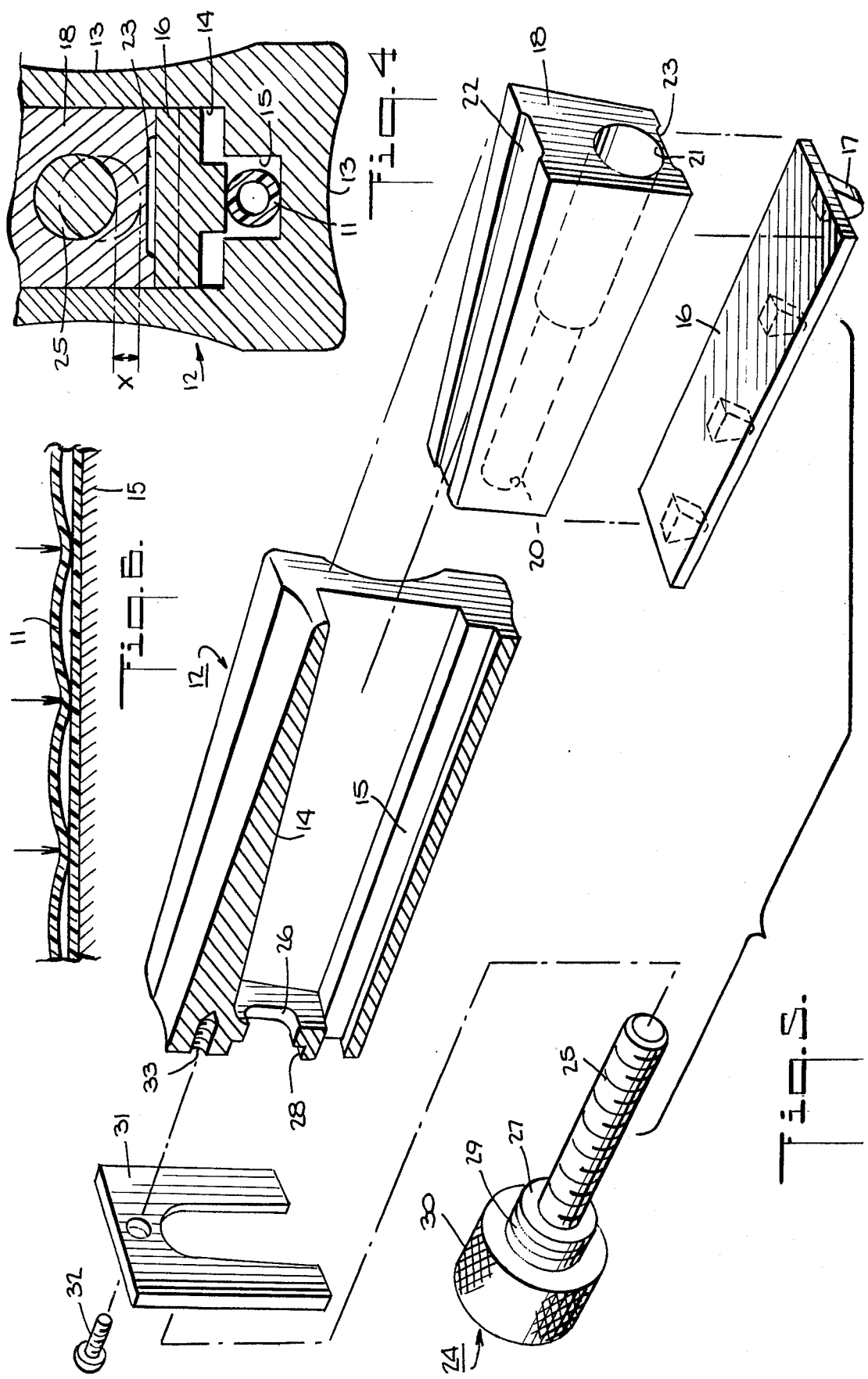

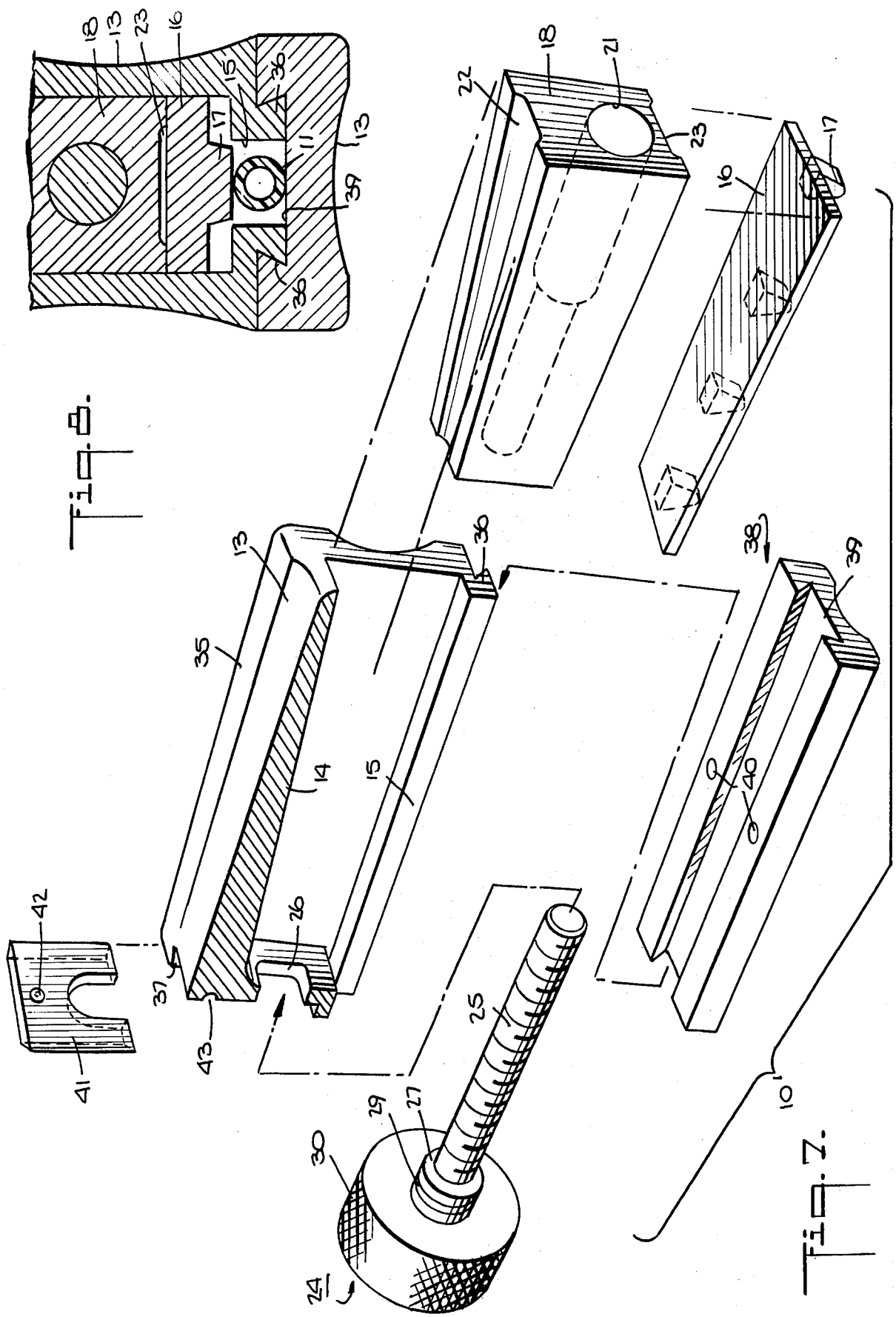

LINEAR METERING VALVE FOR TUBES

This invention relates to a linear metering valve for flexible tubing. More particularly, this invention relates to a reusable valve for intravenous tubing.

As is known, various types of apparatus have been used to supply intravenous fluids to a patient. Generally, these apparatus have employed bottles or pouches of fluid which dispense a flow under gravity via a flexible tube to the patient. In order to control the rate of flow, use has been made of flow adjusting clamps located at selected positions of the tube. However, in many cases, these clamps have required the use of two hands for operation so that a medical attendant has not been free to perform other tasks for a patient. Further, the clamps have frequently been constructed of a pinch type wherein the tube is pinched off at one point to vary the flow. However, in such cases, clogging may occur with a resultant variation in the flow rate which must be continuously readjusted. As a result, a fine metering of the fluid cannot be accomplished without providing auxiliary equipment to prevent frequent clogging and variations in flow rate.

Heretofore, various types of valves have been known for regulating flow, for example as described in U.S. Pat. Nos. 2,582,917 and 4,171,006. In the former case, the valves have not been capable of full shut-off. In the latter case, the valves have required a tubing carrying a fluid flow to be coiled about a central axis within the valve. Further, set-up of such a valve can be cumbersome for a medical attendant, particularly if there is a reason for setting up in a minimum of time.

Accordingly, it is an object of this invention to provide a metering valve which can easily be manipulated in one hand by a user.

It is another object of this invention to provide a metering valve which can be rapidly set up for controlling flow through flexible tubing.

It is another object of this invention to provide a metering valve which will not clog and will offer infinitely variable control of fluid flow from zero to full flow depending upon the cross-section and the resilience of the tubing employed.

It is another object of this invention to provide a linear metering valve which can be readily constructed in an economical manner.

It is another object of this invention to provide a metering valve of simple construction.

Briefly, the invention provides a linear metering valve for flexible tubing, such as tubes for supplying intravenous or like fluids to a patient. The valve comprises a housing defining a passageway for a flexible tubing; a bar means which is movably disposed in the passageway and which has a plurality of protuberances for engaging the tubing; and means for moving the bar means longitudinally within the housing for selectively opening and closing the tubing in order to control the pasage of a fluid therethrough.

The housing may be made of any suitable material, such as plastic resin, and is of generally rectangular cross-sectional shape with contoured side walls sized to be manually manipulated in one hand. In one embodiment, the housing is constructed in one piece such that the tubing is slid longitudinally into and through the housing passageway from one end to the other. In another embodiment, the housing is of multi-piece construction such that one piece of the housing can be fitted over a tubing and a second piece slid or fitted into place to close the tubing within the passageway.

The bar means includes an elongated platten having the protuberances thereon and a draw bar which is slidably engaged with the platten. In this case, the moving means is connected to the draw bar in order to move the bar within the housing to a closed position relative to the tubing. Further, the platten, draw bar and housing passageway are shaped relative to each other in order to cause the platten to progressively engage the tubing laterally on movement of the draw bar to the closed position. For example, the draw bar may be wedge-shaped. In addition, the housing passage has a reduced portion extending longitudinally for receiving the tubing while the protuberances are disposed along the platten to fit into the reduced portion of the passageway.

The moving means may be in the form of a lever or a spindle which is rotatably mounted in the housing for moving the draw bar longitudinally of the housing in response to rotation of the spindle. For example, the spindle may be threaded into the draw bar in order to move the draw bar longitudinally during rotation of the spindle. Rotation of the spindle may be effected manually or automatically. For example, an automatic adjustment may be made using appropriate electronic circuitry, e.g., a calibrated stepping motor may be employed to rotate the spindle by means of a remote signal obtained from another location or by remote radio control.

A retainer is also provided for retaining the spindle coaxially of the housing. This retainer may be separately secured to the housing or may be an integral part of the housing.

The valve is particularly suitable for flexible tubes which are radially deformable, for example being made out of a plastic.

The various parts of the valve can be made of any suitable material, such as plastics which are compatible for the use to which the valve is to be used, for example for metering intravenous fluids.

In order to use the valve, the valve is positioned over a length of tubing at an appropriate intermediate point of the tubing. The spindle is then rotated so that the platten exerts a slight friction grip on the tubing in order to hold the valve in place. Thereafter, while holding the valve in one hand, the spindle can be rotated using the thumb and forefinger to progressively close or open the tubing to a flow of fluid until such time as a desired rate of flow is obtained.

Because the valve uses a plurality of protuberances, for example of generally triangular cross-sectional shape, for pinching off the tubing, a fine metering of the flow can be obtained, for example as described in U.S. Pat. No. 4,071,006.

These and other objects and advantages of the invention will become more apparent from the following detailed description taken in conjunction with the accompanying drawing wherein:

FIG. 1 illustrates a perspective view of a linear metering valve according to the invention in place on a deformable length of tube;

FIG. 2 illustrates a cross-sectional view taken on line 2—2 of FIG. 1 showing the valve in a fully open position;

FIG. 3 illustrates a view similar to FIG. 2 showing the valve in a fully closed position;

FIG. 4 illustrates a cross-sectional view taken on line 4—4 of FIG. 2;

FIG. 5 illustrates an exploded view of the valve of FIG. 1;

FIG. 6 schematically illustrates the manner in which a flexible tubing is pinched off;

FIG. 7 illustrates an exploded view of a modified valve in accordance with the invention; and FIG. 8 illustrates a cross-sectional view of the valve of FIG. 7.

Referring to FIG. 1, the linear metering valve 10 is adapted for use with a deformable flexible tubing or tube 11, for example for delivering intravenous fluid to a patient by means of an intravenous administration assembly. The tubing 11 may carry a flow in either of two axial directions.

Referring to FIGS. 1 and 5, the valve 10 includes a housing 12 of generally rectangular cross-sectional shape with side walls having rounded recesses 13 extending longitudinally thereof and rounded edges to offer a comfortable grip to the user. The housing 12 is sized to be manually manipulated in one hand. For example, the housing 12 has an overall length of about $2\frac{7}{8}$ inches, a width of $\frac{5}{8}$ inch and a height of 1 7/32 inches.

As shown in FIG. 5, the housing 12 includes an internal passageway 14 which is of tapered shape and has a reduced portion 15 in the bottom, as viewed. As shown in FIG. 4, this reduced portion 15 extends throughout the length of the housing 12, and is sized to receive the tube 11, for example in a free-fit relation, i.e., with the tube 11 slightly spaced from the side walls of the reduced portion 15.

The valve 10 also has a bar means movably disposed in the passageway 14 for engaging the tube 11. This bar means includes an elongated platten 16 having a plurality of protuberances 17 spaced along the bottom and a draw bar 18. The platten 16 is loosely mounted in the housing 12 above the reduced passageway portion 15 while the draw bar 18 is slidably mounted between the sidewalls of the passageway 14. Each of the protuberances 17 is of triangular cross-sectional shape with a blunt apex defining an angle of 60° and is of a width sufficient to fit within the reduced portion 15 of the passageway 14 (see FIG. 4). For example, for a tubing 11 having a 1/16 inch inside diameter (I.D.) with a $\frac{1}{8}$ inch outside diameter (O.D.), the protuberances 17 are spaced apart, for example on a pitch of $\frac{1}{8}$ inch and each has a height of approximately 3/32 inch. The draw bar 18 slidably engages the platten 16 and is of generally wedge-shape conforming to the shape of the passageway 14. As indicated in FIG. 2, the top surface of the draw bar 18 is tapered to slide along a corresponding tapered surface of the passageway 14. The draw bar 18 is sized so as to move longitudinally within the housing 12 passageway 14 and may be provided with a depending flange (not shown) to act as a stop for the platten 16.

As shown in FIG. 5, the draw bar 18 has a threaded bore 20 which is longitudinally disposed at one end and an unthreaded counter-bore 21 extending from the bore 20 to the opposite end. The draw bar 18 is also provided with friction-relief grooves 22, 23 along the top and bottom as viewed.

Referring to FIG. 2, the valve 10 has a means for moving the draw bar 18 of the bar means longitudinally within the housing 12 for selectively opening and closing the tube 11 in order to control the passage of fluid therethrough. This means includes a spindle 24 which is rotatably mounted in the housing 12 for moving the draw bar 18 longitudinally in response to rotation of the spindle 24. As indicated in FIGS. 2 and 5, the spindle 24 has a threaded shank 25 which passes through an enlarged opening 26 in the end wall of the housing 12 and threads into the threaded bore 20 of the draw bar 18, a collar 27 which abuts against a recess 28 in the end wall of the housing 12, an annular recess 29 adjacent the collar 27 and a knurled head 30 at the end of the spindle.

The spindle 24 is threaded into the draw bar 18 so as to move the draw bar 18 between a fully open position (FIG. 2) and a fully closed position (FIG. 3). For example, the longitudinal stroke of the draw bar 18 is about 9/16 inch while the resulting transverse (vertical as viewed) stroke is approximately 1/16 inch. During a closing stroke, the platten 16 is pushed downwardly so that the protuberances 17 move into the reduced portion 15 of the passageway 14 and pinch off the tube 11 at a multiplicity of points. This provides a fine metering action on the tube 11, for example as described in U.S. Pat. No. 4,171,006.

In addition, a retainer 31 in the form of a U-shaped plate (see FIG. 5) is secured to the end wall of the housing 12 via threaded screws 32, e.g. three which pass into threaded bores 33 in the housing 12. This retainer 31 fits into the recess 29 of the spindle 24 in order to retain the spindle coaxially of the housing 12 during rotation of the spindle 24 with a minimum of longitudinal movement when reversing the direction of rotation.

As indicated in FIG. 2, the opening 26 in the housing 12 which receives the spindle 24 is elongated to permit the spindle 24 and draw bar 18 to move vertically, as viewed, within the housing 12 during rotation of the spindle 24. Likewise, the recess 28 receiving the collar 27 of the spindle 24 is elongated to accommodate the movement X (FIG. 4) of the collar 27 and the collar 27 is sized relative to the retainer 31 to accommodate this motion.

A cover plate 34 (see FIGS. 1-3) is fitted or otherwise secured as by screws (not shown) to the opposite end of the housing 12 from the spindle 24 in order to retain the draw bar 18 and platten 16 within the passageway 14.

The various components of the valve 10 can be made of any suitable materials. For example, each component may be made of an engineering plastic, for example an acetal plastic resin. Likewise, the tube 11 may be of any suitable material, for example a PVC plastic. Further, the tube 11 may be of any suitable size, for example with a $\frac{1}{8}$ inch outer diameter and an inside diameter of 1/16 inch, to fit into the reduced passageway portion 15.

In use, the valve 10 is slid over the flexible tube 11 and located at an appropriate position. If necessary, the spindle 24 may then be rotated a partial turn to draw the draw bar 18 into the housing 12 so that the platten 16 engages the tube 11 with a slight friction in order to hold the valve 10 in place. When fluid passing through the tube 11 is to be metered, the spindle 24 is turned so that the draw bar 18 moves further into the housing 12 and forces the platten 16 transversely (vertically as viewed) into the reduced portion 15 of passageway 14 against the tube 11. This causes the protuberances 17 to compress the tube 11 at spaced apart points and, thus progressively close off the tube 11 for a sensitive metering action.

Referring to FIG. 6, the compressing of the tube 11 at a multiplicity of points causes a like multiplicity of orifices to form in the tube 11. Further, at each orifice, a venturi-action occurs which tends to cleanse the flow path at various flow rates. As indicated, changes in each orifice (aperture) vary the relative velocity of the fluid when transferring from a large cross-sectional area (i.e. large volume-slow velocity-laminar flow) to a smaller cross-sectional are (i.e. small volume-high velocity turbulent flow), increasing the velocity at the smaller orifices. This serves to cleanse obstructions in the fluid path and allows a straight-through processing of the controlled fluid.

If complete closure is required, the spindle 24 is rotated so that the draw bar 18 forces the protuberances 17 on the platten 16 further against the tube 11 so that the tube closes, for example as illustrated in FIG. 3. In this fully closed position, no flow of fluid occurs through the tube 11.

In order to open the tube, the spindle 24 is rotated in an opposite direction so that the draw bar 18 moves in a direction out of the housing 12 (see FIG. 2). This allows the resilience of the tube 11 and the pressure of the fluid to open the tube 11 to flow and to lift the platten 16.

Referring to FIGS. 7 and 8, wherein like reference characters indicate like parts as above, the metering valve 10' may alternatively be constructed to fit over a tubing 11 in a transverse manner. To this end, the valve 10' has a housing of multi-piece construction with one piece 35 defining a main portion having a passageway 14 and a reduced portion 15 for passage of a tubing 11. This housing piece 35 has a pair of elongated ribs 36 along the bottom, as viewed, which cooperate to define a dove-tail shaped tongue as well as a dove-tailed slot 37 at one end. A second housing piece 38 is in the form of a slide having a longitudinal slot 39 which is sized to slidably receive the tongue (ribs 36) of the housing piece 35. The slider piece 38 thus acts as a cover for the reduced portion 15 and may also have a pair of small recesses 40 for receiving a pair of protuberances (not shown) on the housing piece 35 in a snap-lock manner.

In addition, a retainer 41 in the form of a small U-shaped plate of trapezoidal cross-section is slidably mounted in the slot 37 of the main housing piece 35. This plate-like retainer 41 has a protuberance 42 for snapping into a recess 43 in the housing piece 35 within the slot 37 in a snap-lock manner.

The housing piece 35 houses a platten 16 and a draw bar 18 as above and cooperate with a threaded spindle 24.

In use, in order to mount the valve 10' on a tubing 11, the slider piece 38 is slid off the main housing piece 35. Next, the main housing piece 35 is fitted over the tubing 11 so that a length of the tubing fits into and along the reduced portion 15. The slider piece 38 is then slid over the tongue (ribs 36) and snapped into place via the recesses 40. Metering of a flow through the tubing 11 is then controlled as above.

By using the slidable plate-like housing piece 41, the use of screws can be eliminated. This permits the valve 10' to be assembled in a more rapid manner. Likewise, by using the slider piece 38, the need for "threading" tubing 11 through the valve housing is eliminated. This allows the valve 10' to be reusable and allows the valve 10' to be applied to any permanent installation where both ends of the tubing have, for example, sterilized protuberances.

The invention thus provides a linear metering valve which can be readily manipulated in one hand for opening and closing a deformable tubing, for example for feeding intravenous fluids to a patient with the use of an intravenous administration set as is used in the medical field.

The invention further provides a valve which can be simply constructed of a minimum of parts and which can be readily positioned on a tube for use in metering a flow through the tube.

The invention further provides a multiple-orifice flow valve wherein venturi-action occurs at each orifice which tends to cleanse the flow path at various flow rates. In addition to obtaining a bubble-free closure, the valve allows an infinitely variable flow to be obtained, for example from less than one drop per minute to full flow depending upon the resilient nature of the flexible tube employed.

The valve is not limited in size or for only the medical field. That is, the valve can be larger or smaller and controlled electrically or electronically, i.e. via a stepping motor receiving a signal from a remote push-button, or with radio control circuitry. As an example, should drops of radioactive materials be required in an insulated environment, the valve spindle can be operated from a remote location.

The valve may also be used to control air, gases, liquids, slurries and the like, for example in dispensing controlled volumes of paint, coloring or other chemicals.

The valve can be constructed of any suitable material. Of note, as the tubing carries the fluid or gas to be controlled, the valve is subject to ambient conditions only and is not subject to corrosion via the controlled fluid or gas.

What is claimed is:

1. A linear metering valve for flexible tubing comprising
    housing defining a longitudinal passageway having a reduced portion for slidably receiving a flexible tubing therein;
    a bar means movably disposed in said passageway of said housing, said bar means having a plurality of longitudinally spaced protuberances thereon sized to fit into said reduced portion for engaging the tubing passing through said housing passageway; and
    means for moving said bar means longitudinally and transversely within said passageway of said housing for selectively opening and closing the tubing to control the velocity of a fluid therethrough.

2. A linear metering valve as set forth in claim 1 wherein said bar means includes an elongated platten having said protuberances thereon and a draw bar slidably engaging said platten.

3. A linear metering valve as set forth in claim 2 wherein said draw bar is wedge-shaped.

4. A linear metering valve as set forth in claim 1 wherein said housing is of generally rectangular cross-sectional shape and is sized to be manually manipulated in one hand.

5. A linear metering valve as set forth in claim 1 wherein said housing is of multi-piece construction and includes a main portion defining said passageway and a slider slidably mounted in said main portion to cover a tubing in said passageway.

6. A linear metering valve as set forth in claim 5 wherein said moving means is a spindle rotatably mounted in said housing for moving said bar means longitudinally of said housing in response to rotation of said spindle.

7. In combination,
an elongated flexible radially deformable tubing and
a manually operable linear metering valve for controlling a flow through said tubing, said valve including a housing defining a longitudinal passageway having a reduced portion receiving said tubing passing therethrough in slidable parallel relation, a bar means having a plurality of longitudinally spaced protuberances for engaging said tubing in said passageway and means for moving said bar means longitudinally and transversely within said passageway of said housing for closing said protuberances on said tubing to control the flow therethrough.

8. The combination as set forth in claim 7 wherein said bar means includes an elongated platten having said protuberances thereon and a draw bar slidably engaging said platten, said moving means being connected to said draw bar to move said draw bar longitudinally within said housing to a closed position relative to said tubing; said platten, said draw bar and said housing passageway being shaped relative to each other to cause said draw bar to move said platten transversely to progressively engage said tubing upon movement of said draw bar to said closing position.

9. The combination as set forth in claim 7 wherein said housing is of multi-piece construction and includes a main portion defining said passageway and a slider slidably mounted in said main portion to cover a tubing in said passageway.

10. A linear metering valve for flexible tubing comprising
a housing defining a passageway wedgeshaped for a flexible tubing;
an elongated platten disposed in said passageway to move transversely of said passageway and having a plurality of protuberances thereon for engaging the tubing passing through said housing passageway;
a wedge-shaped draw bar slideably engaging said platten; and
means connected to said draw bar to move said draw bar longitudinally and transversely within said housing to cause said platten to move transversely of said passageway for selectively opening and closing the tubing to control the velocity of a fluid therethrough.

11. A linear metering valve as set forth in claim 10 wherein said housing passage has a reduced portion extending longitudinally thereof for receiving a tube therein and said protuberances are disposed along and sized to fit into said reduced portion.

12. A linear metering valve for flexible tubing comprising
a housing defining a passageway for a flexible tubing;
an elongated platten movably disposed in said passageway and having a plurality of protuberances thereon for engaging the tubing passing through said housing passageway;
a draw bar movably disposed in said passageway and slidably engaging said platten; and
means for moving said bar longitudinally within said housing to a closed position relative to the tubing for selectively opening and closing the tubing to control the velocity of a fluid therethrough, said platten, said draw bar and said housing passageway being shaped relative to each other to cause said platten to move transversely of said passageway to progressively engage the tubing upon movement of said draw bar to said closed position.

13. A linear metering valve as set forth in claim 12 wherein each of said passageway and said draw bar is wedge-shaped whereby said draw bar moves transversely of said passageway during longitudinal movement.

14. A linear metering valve as set forth in claim 1 wherein said moving means is a spindle rotatably mounted in said housing for moving said bar longitudinally and transversely of said housing in response to rotation of said spindle.

15. A linear metering valve as set forth in claim 14 which further comprises a retainer for retaining said spindle coaxially of said housing.

16. A linear metering valve as set forth in claim 12 wherein said platten is loosely mounted in said housing.

* * * * *

UNITED STATES PATENT AND TRADEMARK OFFICE
CERTIFICATE OF CORRECTION

PATENT NO. : 4,456,030
DATED : June 26, 1984
INVENTOR(S) : Armen Bogossian

It is certified that error appears in the above-identified patent and that said Letters Patent is hereby corrected as shown below:

| Column | Line | Correction/Change From | To |
|--------|------|------------------------|------|
| 1 | 59 | "pasage" | -- passage -- |
| 5 | 6 | "are" | -- area -- |

Signed and Sealed this

Twenty-fifth Day of December 1984

[SEAL]

Attest:

*Attesting Officer*

GERALD J. MOSSINGHOFF

*Commissioner of Patents and Trademarks*